United States Patent [19]

Amino et al.

[11] Patent Number: 5,549,684
[45] Date of Patent: Aug. 27, 1996

[54] ARTIFICIAL KNEE JOINT

[75] Inventors: Hirokazu Amino, Kyoto, Japan; Ian C. Clarke, Santa Monica, Calif.

[73] Assignee: Kyocera Corporation, Kyoto, Japan

[21] Appl. No.: 147,412

[22] Filed: Nov. 5, 1993

Related U.S. Application Data

[63] Continuation of Ser. No. 50,758, Apr. 20, 1993, abandoned, which is a continuation of Ser. No. 939,835, Sep. 2, 1992, abandoned, which is a continuation of Ser. No. 632,321, Dec. 21, 1990, abandoned.

[30] Foreign Application Priority Data

Dec. 26, 1989 [JP] Japan .................................... 1-337829
Dec. 26, 1989 [JP] Japan .................................... 1-337830

[51] Int. Cl.⁶ .................................................... A61F 2/38
[52] U.S. Cl. .................................................. 623/20; 623/18
[58] Field of Search ............................... 623/16, 18, 20

[56] References Cited

U.S. PATENT DOCUMENTS 4,355,429 10/1982 Mittelmeier et al. ..................... 623/20
4,728,332 3/1988 Albrektsson ............................ 623/20
4,959,071 9/1990 Brown et al. ..

FOREIGN PATENT DOCUMENTS 0268216 5/1988 European Pat. Off. .................. 623/20
0294298 12/1988 European Pat. Off. ..

*Primary Examiner*—David Isabella
*Attorney, Agent, or Firm*—Loeb & Loeb LLP

[57] ABSTRACT

An artificial knee joint comprising a femur member to be secured to the distal portion of a femur and a tibia member to be secured to the proximal portion of a tibia, wherein the femur member is made of alumina ceramics or zirconia ceramics, and the tibia member is a combination of a sliding section made of high-density polyethylene and a seat section made of titanium, titanium alloy, cobalt-chromium alloy or stainless steel.

With this joint, the service life of the tibia member can be extended significantly. This disclosure also includes a modified embodiment of the above-mentioned artificial knee joint that includes reinforcing ribs with a special cross sectional shape to increase resistance against bending force applied to the femur member.

4 Claims, 3 Drawing Sheets

1

ARTIFICIAL KNEE JOINT

This is a continuation of application Ser. No. 08/050,758 filed Apr. 20, 1993, now abandoned, which is a continuation of application Ser. No. 07/939,835 filed Sep. 2, 1992 also abandoned, itself in turn a continuation of application Ser. No. 07/632,321 filed Dec. 21, 1990, also now abandoned.

BACKGROUND OF THE INVENTION

1. Field of the Invention

The present invention relates to the improvements of an artificial knee joint used in orthopedic treatment to restore knee joints significantly deformed by rheumatism or osteoarthritis and causing pain and difficulty in walking, or those broken (or damaged) by bone tumor or by traumatic injuries incurred in traffic accidents or during sporting activities.

2. Prior Art

Artificial knee joints have been studied and used practically just recently. Like an artificial hip joint, an artificial knee joint receives flexion and extension movement loads on its joint surfaces while sliding during walking or physical exercise; the artificial knee joint thus functions as a load receiving joint. Since joint problems and breakage are caused frequently by diseases or traumatic injuries, cases of replacing and restoring knee joints using artificial knee joints have been increasing steadily these days. A typical structure of an artificial knee joint is shown in FIG. 1. The joint comprises a femur member A secured to the lower end surface (distal surface) of a femur F and a tibia member B secured to the upper end section (proximal tibia) of a tibia T. The member A integrally comprising a joint front wall al being upright on the front side, a couple of joint condyles a2, a2 that are gradually extended backward in a nearly arced shape to slide on the concave joint surface b2 of the sliding section b1 of a tibia member B, and joint rear walls a3, a3 being upright in an acute arced shape behind the joint condyles a2, a2. The tibia member B comprises the above-mentioned sliding section b1, the concave joint surface b2 formed on the sliding section b1, and an embedding section b3 to be secured in a proximal canal of the tibia T. The distal end of the femur F is cut off and the femur member A is attached to the femur F by using bone cement. The tibia member B is embedded and secured to the upper end (proximal end) of the tibia T. The joint surface b2 of the sliding section b1 slidably receives mainly the joint condyles a2, a2 (when the knee is bent and stretched slightly) or slidably receives both the joint condyles a2, a2 and the joint rear walls a3, a3 (when the knee is bent sharply) to allow the knee to be bent and stretched. FIGS. 2A and 2B are perspective views illustrating the members A and B separated from the knee joint shown in FIG. 1. In the case of the above-mentioned conventional artificial knee joint, the sliding section b1 is made of HDP (high-density polyethylene) to highly slidably receive the member A and needs a seat section b4 (see FIG. 2B) for reinforcement.

Both the members A and B of the conventional artificial knee joint are made of a metal harmless to a living body, such as pure titanium, titanium alloy or cobalt-chromium alloy, or made of a ceramics harmless to a living body, such as alumina ceramics or zirconia ceramics. Such metal and ceramics materials have both their advantages and disadvantages. When made of metal, the seat section b4 can have relatively high resistance against impact stress even if it is thin. When made of ceramics, however, the seat section b4 should be twice as thick as that made of metal to obtain the same impact strength as that of the seal section b4. In view of the amount of wear, the joint surface b2 of the sliding section b1 made of metal wears more significantly when it contacts the femur member A made of metal than when it contacts the femur member A made of ceramics. If the total thickness of the sliding section b1 and the seat section b4 of the tibia member B is made larger, the cutting amount of the tibia T must also be made larger. This is not desirable from the orthopedic surgery point of view. Taking these into consideration, the thickness of the sliding section b1 is set to 8 mm. A first problem to be solved is how to increase the service life of the tibia member B while the thickness of the sliding section B1 is limited to 8 mm. The femur member A made of metal is combined with the tibia member B made of metal, or the femur member A made of ceramics is combined with the tibia member B made of ceramics. Each combination has its advantages and disadvantages. In particular, the femur member A made of ceramics is inherently weak in resistance against a dynamic load transmitted from the femur F mainly in the vertical direction, that is, external force exerted to the internal sections of the joint condyles a2, a2 of the femur member A to slide the femur member A on the sliding section b1. To solve this problem, a pair of reinforcing ribs a4 with nearly horizontal upper edges are formed in parallel as shown in FIGS. 2A and 3. The strength of the femur member A made of ceramics against the above-mentioned external force can be approximated to the value obtained in the bending strength test shown in FIG. 4. The test is conducted in the manner described below. The femur member A is placed upside down on a support D and secured to it by using cement C. Load E is gradually applied to the member A from above to exert force so that the member A is bent outward (forward and backward). The bending strength of the member is obtained by measuring the load applied at the point the internal surface of the member A is cracked or broken. In this kind of test, cracks and breakage are apt to appear near a connection section all between the reinforcing rib a4 and the joint front wall al. This means that bending stress is concentrated at the portion. When the knee joint is bent sharply, bending stress is concentrated at the connection section a31 located on the rear side of the rib a4. In this case, the joint rear wall a3 slides on the joint surface b2 to receive the external bending force. If any crack or breakage occurs inside the femur member A of the artificial knee joint as described above, the joint may not function or bone breakage may occur, resulting in a serious danger.

This is a second problem to be solved; bone breakage accidents and obstacles against smooth joint movement need to be eliminated by increasing the bending strength of the femur member.

SUMMARY OF THE INVENTION

The object of the present invention is to provide an artificial knee joint that can solve the above-mentioned first and second problems.

The object of a first invention to solve the first problem is to extend the service life of the artificial knee joint by decreasing the thickness of the seat b4 as small as possible and by increasing the thickness of the sliding section b1 by the amount corresponding to the decrease in the thickness of the seat b4.

To solve the second problem, the inventors of the present invention contrived various means to improve the bending brittleness of the conventional reinforcing ribs. The most primitive means is to increase the thickness and height of the ribs. In the case of this means, the rib support groove holes of the femur F must be made larger. This increases the amount of the natural bone to be cut off and is not desirable from the view point of surgeons. Through trial and error, the inventors succeeded in increasing the bending breakage strength of the reinforcing rib a4 by more than 200%, not by increasing the thickness of the reinforcing rib a4, but by gradually distributing a dynamic critical cross section that was conceived when a load was applied, instead of concentrating the cross section at one portion, in other words, by making the reinforcing rib a4 into a form having no abrupt cross section when coping with a bending load at the inner cavity of the member A. Accordingly, the second invention is achieved.

The first and second inventions are detailed below referring to the attached drawings.

DETAILED DESCRIPTION OF THE INVENTION

Figure 1:
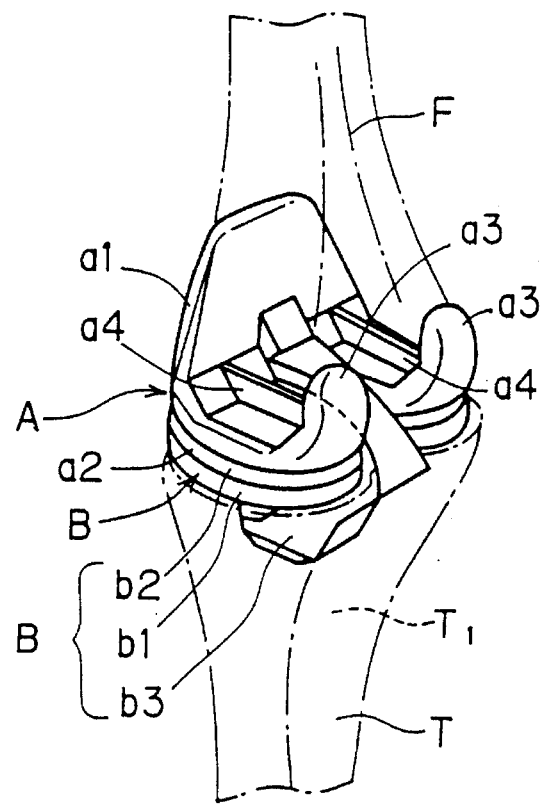
FIG. 1 is a perspective view illustrating an installation condition of a conventional artificial knee joint.

The first invention relates to an artificial knee joint comprising a femur member A to be secured to the distal portion of a femur F and a tibia member B to be secured to the proximal portion of a tibia T, wherein the femur member A is made of alumina ceramics or zirconia ceramics, and the tibia member B is a combination of a sliding section b1 made of high-density polyethylene and a seat section b4 made of titanium, titanium alloy, cobalt-chromium alloy or stainless steel.

The joint condyle a2 of the femur member A made of ceramics and brought into contact with the joint surface b2 has a surface roughness of 0.2 μ or finer.

EXAMPLE 1

The amount of wear at the joint surface b2 of the sliding section b1 of the tibia member B, which slidably receives the joint condyles a2, a2 and the joint rear wall a3, a3 of the femur member A made of ceramics under a large load, is examined as described below. The amount of wear at the joint surface b2 of the joint with the relative material combination of ceramics and high-density polyethylene is significantly lower than that at the joint surface b2 of the joint with the relative material combination of metal and high-density polyethylene. The amount of wear at the joint surface b2 that supports the femur member A made of alumina ceramics, for example, is about 1/10 of the amount of wear at the joint surface b2 that supports the femur member A made of metal. The seat b4 under the sliding section b1 has high impact resistance since it is made of titanium alloy. Therefore, the seat b4 can be made as thin as possible (2 mm for example) to the extent that its support effect is maintained, and the sliding section b1 can be made thicker by the amount corresponding to the decrease in the thickness of the seat b4 [from 4 mm (original thickness) to 6 mm for example]. As a result, the service life of the sliding section b1 can be significantly extended. Since the amount wear at the sliding section b1 is assumed to be 0.2 mm/year for normal knee movement when an artificial knee joint made of metal is used for example, the service life of this embodiment would be enormous when simply estimated, due to the above-mentioned significant reduction of the amount of wear and the increased thickness of the sliding section b1.

In the case of the above-mentioned first invention, the service life of the tibia member can be extended significantly by using the femur member made of ceramics and the tibia member (except for the sliding section) made of metal, as clearly described above. This extended service life is extremely beneficial to patients.

The second invention is an artificial knee joint comprising the above-mentioned femur member that includes a joint front wall al being upright on the front side, a couple of joint condyles a2, a2 gradually extended backward in a nearly arced shape, joint rear walls a3, a3 being upright in an acute arced shape behind the joint condyles a2, a2, and a pair of reinforcing ribs a4, a4 disposed inside the joint condyles a2, a2 in the joint movement direction, wherein the upper edge a5 of the reinforcing rib a4 has a shape that is similar to the inner circumferential shape of the femur member A formed by the inner walls of the joint front wall al, joint condyle a2 and joint rear wall a3 so that a connection section a6 is formed from the joint front wall al and the joint rear wall a3 to the reinforcing rib a4 to gradually increase the vertical sectional area of the connection section a6, the femur member A of the second invention is made of the same material as that of the femur member A of the first invention, and the tibia member B of the second invention is also made of the same material as that of the tibia member B of the first invention.

The typical ceramics material for the femur member A is alumina ceramics or zirconia ceramics, and the typical metal for the tibia member B is pure titanium, titanium alloy, cobalt-chromium alloy or stainless steel.

EXAMPLE 2

Figure 3:
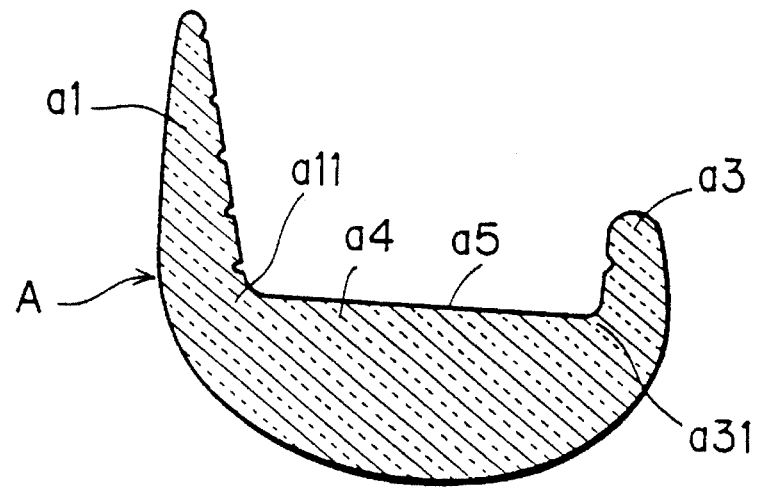
FIG. 3 is a vertical sectional view taken at the reinforcing rib of the conventional artificial knee joint.
Figure 5:
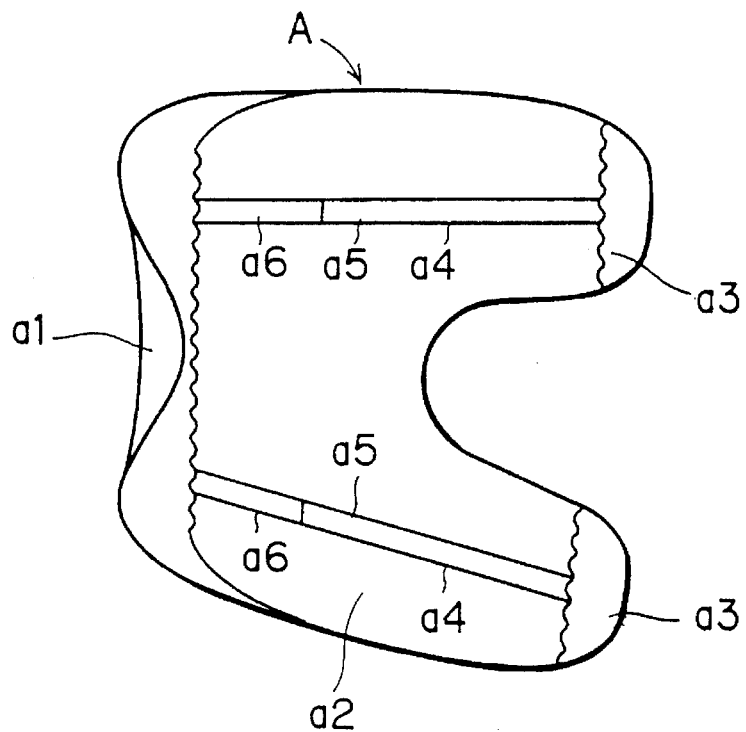
FIG. 5 is a plan view of the femur member of the second invention.
Figure 6:
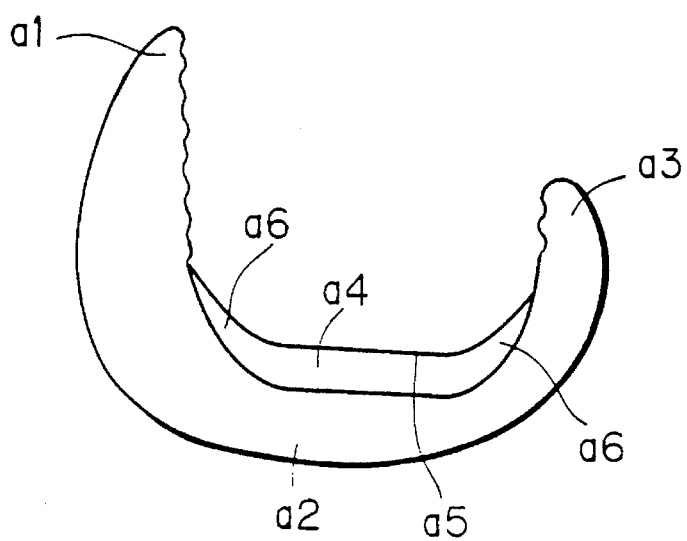
FIG. 6 is a side view of the femur member of the second invention.

Referring to the example shown in FIGS. 5 and 6, the upper edge a5 of each reinforcing rib a4 has a shape that is similar to the inner circumferential shape of the femur member A formed by the inner walls of the joint front wall al, joint condyle a2 and joint rear wall a3 so that the connection section a6 is formed from the joint front wall al and the joint rear wall a3 to the reinforcing rib a4 to gradually increase the vertical sectional area of the connection section a6. More particularly, unlike the conventional shape of the reinforcing rib a4 shown in FIG. 3, which has an abruptly changing vertical sectional area from the joint front wall al and the joint rear wall a3 to the reinforcing rib a4, the form of the reinforcing rib a4 of the second invention has a gradually increasing vertical sectional area. In other words, when the connection sections all and a31 at the front and rear ends of the reinforcing rib a4 are assumed to be critical sectional areas for a bending load in FIG. 3, such a critical sectional area is not concentrated at any vertical single portion along the length of the reinforcing rib a4 in the case of the second invention, but gradually distributed over the entire area of the connection section a6, significantly increasing the resistance against the abovementioned bending load. This feature has been confirmed by the experiment described below.

<Test> i) Object: The femur member having the structure shown in FIGS. 5 and 8
ii) Femur member: Alumina ceramics
iii) Width of the reinforcing rib: 3 mm
iv) Height of the reinforcing rib: 7 mm

Figure 2A:
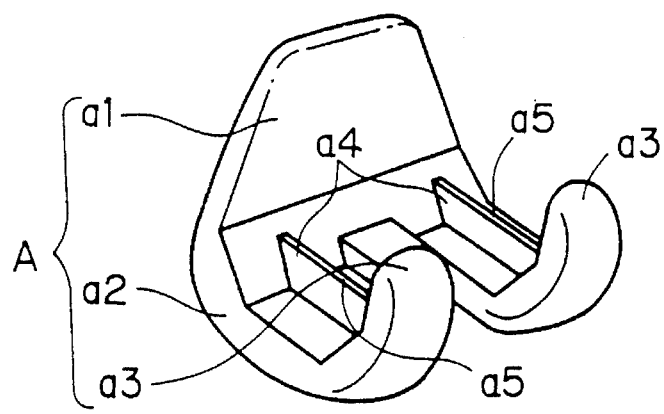
FIGS. 2A and 2B are perspective views illustrating the disassembled members of the conventional artificial knee joint.
Figure 2B:
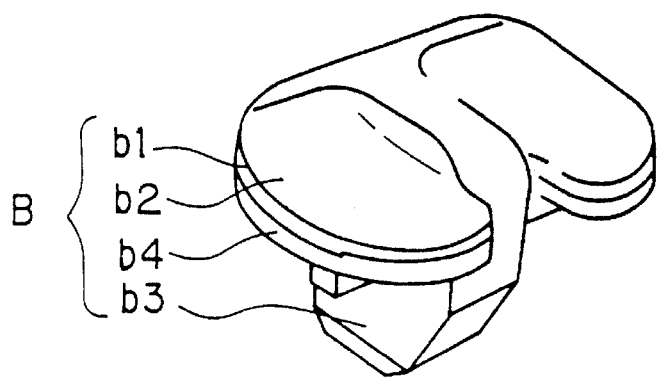
Figure 4:
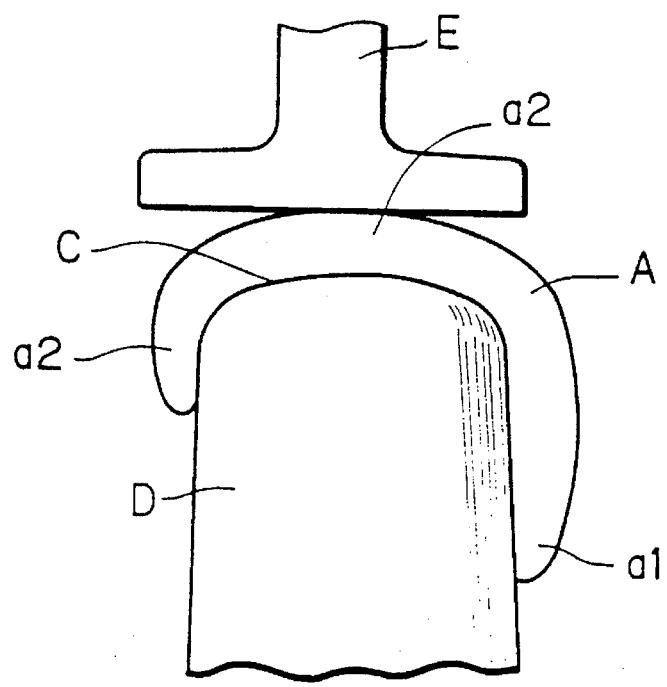
FIG. 4 illustrates a bending load test method.

COMPARISON EXAMPLE i) Object: The femur member having the structure shown in FIGS. 2 and 3 (having the same specifications as those of the embodiment except for the reinforcing rib)
ii) Femur member: Alumina ceramics
iii) Width of the reinforcing rib: 3 mm
iv) Height of the reinforcing rib: 10 mm <Test> i) Test method: The test method conducted as shown in FIG. 4
ii) Results: The comparison example was broken at a load of 2,500 kg, but the embodiment of the second invention was free from cracks even at a load of 5,000 kg (5 tons).

According to the results of the test, the bending strength of the femur member of the second invention is higher by more than 200% than that of the femur member of the conventional joint by providing the connection sections from the joint front wall and the joint rear wall to the reinforcing rib to gradually change the vertical sectional area of the reinforcing rib. Therefore, the embodiment of the second invention is highly beneficial since it can significantly eliminate joint problems and bone breakage.

We claim:

1. An artificial knee joint for a femur having a distal portion and a tibia having a proximal portion, comprising a femur member to be secured to the distal portion of the femur and a tibia member to be secured to the proximal portion of the tibia, wherein said femur member includes an upright joint front wall having an inner surface, a couple of joint condyles gradually extending backward in a generally arced shape and each having a condyle inner surface, a pair of upright joint rear walls each having an inner surface, said rear walls being in an acute generally arced shape behind said joint condyles and a pair of reinforcing ribs each extending from the inner surface of said front wall to the inner surfaces of said rear walls and having an upper edge which substantially follows the contour of an inner circumferential shape defined by the front inner surfaces of said joint front wall, the condyle inner surface of each of said joint condyles and the rear inner surface of each of said joint rear walls, and said femur member is made of one of alumina ceramics and zirconia ceramics, and said tibia member includes a sliding section made of high-density polyethylene and a seat section made of a material selected from a group consisting of titanium, titanium alloy, cobalt-chromium alloy and stainless steel.

2. A femur joint prosthesis for attachment to a knee joint comprising:

an upright front wall having an inner surface;

a pair of condyles having an inner condyle surface connected to said front wall inner surface;

a pair of upright rear walls each having an inner surface connected to said inner condyle surface wherein said front wall inner surface, inner condyle surface and rear wall inner surface define an inner circumferential shape; and a pair of reinforcing ribs each extending from said front wall inner surface to each of said rear wall inner surfaces and having an upper edge which substantially follows the contour of the inner circumferential shape defined by said inner front surface, inner condyle surface and inner rear surface.

3. A bifurcate generally U-shaped femur joint prosthesis for attachment to a knee joint comprising an upright front wall having an inner surface, a bottom wall having a bottom wall inner surface, a pair of upright rear walls each having an inner surface wherein said front wall inner surface, bottom wall inner surface and rear wall inner surface define an inner circumferential shape, and a pair of reinforcing ribs each extending from the front wall inner surface to the rear wall inner surfaces and having an upper edge which substantially follows the contour of the inner circumferential shape of the femur joint prosthesis.

4. An artificial knee joint for a femur having a distal portion, and a tibia having a proximal portion which has a prepared surface having a proximal canal, comprising:

a femur member to be secured to the distal portion of the femur, said femur member including an upright front wall having an inner surface, a pair of joint condyles each having a condyle external surface, and an inner surface which includes a first side, a rear side and generally rounded corners on the front side and rear side of said condyle inner surface, a pair of upright rear walls each having an inner surface, one of the rounded corners on the condyle inner surface front side being connected to the upright front wall inner surface and the other of the rounded corners on the condyle inner surface rear side being connected to the upright rear wall inner surface, wherein said upright front wall inner surface, condyle inner surface and upright rear wall inner surface define an inner circumferential shape, and a pair of reinforcing ribs each extending from the upright front wall inner surface to the upright rear wall inner surfaces and having an upper edge which substantially follows the contour of the inner circumferential shape defined by the inner surfaces of said joint front wall, joint condyle and joint rear walls; and a tibia member, said tibia member including a seat plate to be secured to the prepared surface of the proximal portion of the tibia, said seat member including an embedding protrusion in a central portion thereof which is secured in the proximal canal formed in the prepared surface of the proximal portion of the tibia, and a sliding member provided on said seat member, said sliding member including a pair of concave surfaces for receiving the external condyle surfaces of said femur member.

\* \* \* \* \*